United States Patent [19]
de Medinaceli

[11] Patent Number: 5,122,151
[45] Date of Patent: Jun. 16, 1992

[54] NERVE CONNECTOR AND METHOD

[75] Inventor: Luis de Medinaceli, Alexandria, Va.

[73] Assignee: 501 Ocean Trading, Ltd., Grand Turk, Turks and Caicos Isls.

[21] Appl. No.: 639,969

[22] Filed: Jan. 11, 1991

Related U.S. Application Data

[63] Continuation-in-part of Ser. No. 468,700, Jan. 23, 1990, Pat. No. 4,986,828.

[51] Int. Cl.⁵ ............................................. A61B 17/00
[52] U.S. Cl. ..................................... 606/152; 128/898
[58] Field of Search ..................... 606/152; 128/898

[56] References Cited

U.S. PATENT DOCUMENTS

| | | | |
|---|---|---|---|
| 4,552,145 | 11/1985 | Riley et al. | 128/630 |
| 4,586,504 | 5/1986 | de Medinaceli | 606/152 |
| 4,662,884 | 5/1987 | Stensaas | 606/152 |

Primary Examiner—Stephen C. Pellegrino
Assistant Examiner—Gary Jackson
Attorney, Agent, or Firm—Rosenthal & Putterman

[57] ABSTRACT

A method and apparatus for reconnecting stumps of transected cable-like organs, such as nerves, is disclosed. The apparatus comprises a template and a connector. The connector has inscribed guide lines that indicate proper placement of the nerve stumps for optimum healing. The nerve stumps are connected to the connector, trimmed and the template is removed.

13 Claims, 4 Drawing Sheets

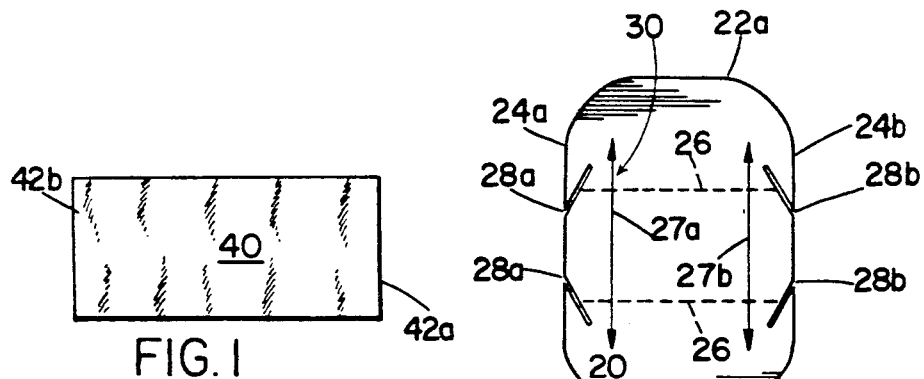
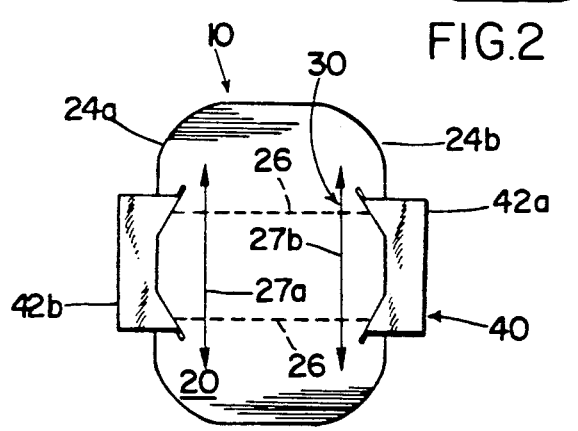
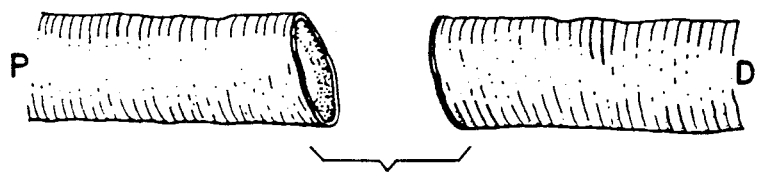
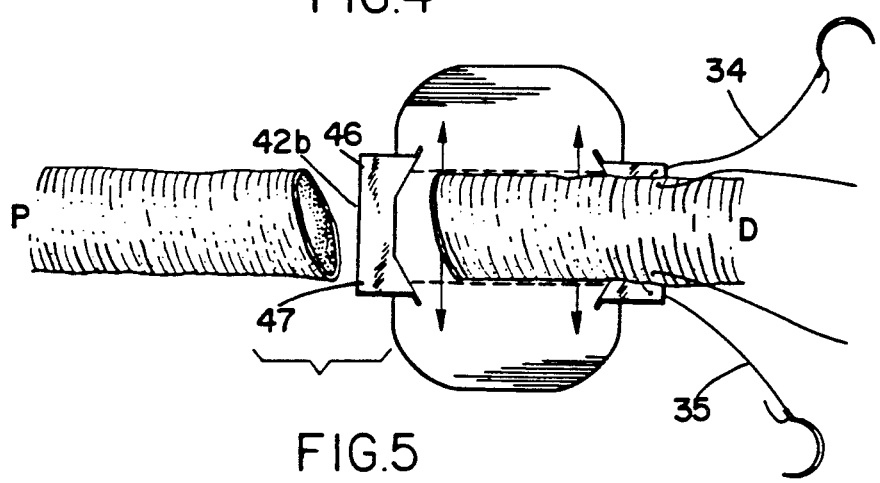

NERVE CONNECTOR AND METHOD

This application is a continuation-in-part of U.S. patent application Ser. No. 87/468,700 filed Jan. 23, 1990, now U.S. Pat. No. 4,986,828, and entitled "Improved Nerve Connector And Method."

FIELD OF THE INVENTION

This invention relates generally to the field of surgery, and more specifically to a method and apparatus for rejoining the proximal and distal stumps of transected cable-like organs such as peripheral nerves.

BACKGROUND OF THE INVENTION

It is known to reconnect transected nerves, blood vessels, tendons and the like using microsurgical techniques. However, using present methods, results are unpredictable and depend on a number of factors including the skill of the surgeon, the type of injury sustained and the time elapsed between the injury and the repair. In addition, while the techniques for rejoining the proximal and distal stumps of the various cable-like organs are substantially analogous to one another, the results vary widely depending on the particular structure being reconnected. This is especially true with respect to nerve fibers where at the zone of a cut, all pathways are destroyed and the ability of the nerve to transmit signals is completely lost. The nerve will sometimes reconnect itself due to the action of neurites that are born in the proximal stump that grow at random in the area of the cut. After suture, most sprouts will reach the distal stump and, therefore, penetrate structures that have not been damaged. From there on, they will follow steadily and blindly the guide that they have found, without branching or changing direction. At the suture line, however, considerable interlacing of the regenerating fibers occurs, so that many neurites fail to enter the appropriate endoneurial tube in the distal stump which results in less than optimal restoration of the motor function.

To decrease the interlacing of regenerating neurites in a transected and repaired nerve, it is necessary to keep the fibers in good longitudinal alignment with their stumps to prevent or at least to minimize whorling of the nerve structures. However, in practice keeping the fibers in longitudinal alignment is quite difficult. Nerve fibers are so soft that the slightest stress disrupts them and modifies their direction. In addition to the whorling problem mentioned above, at the tip of the transected nerve, the additional problems of buckle and wave must be addressed during reconnection. Suturing the stumps considerably worsens the situation because no matter how fine the stitches are, they impart irregular stresses on the nerve. There is a combination of traction at the suture points and of slackness between them. This irregular stress on the nerve sheaths results in a profound longitudinal disorganization of the fibers inside the faciles.

A partial solution to the problem is suggested by U.S. Pat. No. 4,586,504 to de Medinaceli entitled "Nerve Connector and Method." The patent teaches a method and apparatus for obtaining enhanced results when rejoining the proximal and distal stumps of transected cable-like organs, such as nerves, by removing all foreign matter from the zone of reunion thereby equalizing the stresses in the zone. This is accomplished by suturing the nerve stumps in contacting relation on to a template such that the sutures are 1.5-2 diameters away from the zone of reunion according to a postulate derived from the principle of Saint-Venant and discussed in my paper entitled "How to Correctly Match 175,000 Neurites The Postulates For A Quick Solution", BioSystems, Vol 20, pp 307-315, 1987.

More specifically, the de Medinaceli patent teaches a nerve connecting device on which there are transcribed the lines and pattern necessary to make a reunion of the nerve stumps. The lines and pattern indicate the nerve diameter, the general position of the nerve on the device, the distance at which the fixation stitches must be placed from the tip of each stump and the amount of tissue that must be trimmed from the stumps.

To use the prior art de Medinaceli apparatus it was first necessary to assess the diameter of the nerve. This diameter measurement was then confirmed by placing the nerve connector corresponding to the measured diameter beneath the nerve and visually making a determination as to whether the nerve diameter corresponded roughly to the distance between a pair of parallel lines inscribed on the connector. In operation, the sutures were loosely applied to one of the stumps and to the connector. Then the connector was pulled towards the other stump and it was similarly sutured to the connector. Thereafter, the first stump sutures were tightened, stretching the stump and bringing it into overlying relation on top of the connector so that the two stumps laid side-by-side overlapping one another. In the next step, the stumps were trimmed and placed end to end prior to folding over flaps on the template and suturing it closed.

The foregoing system, while effective, was not without its drawbacks as the process of rejoining a transected nerve was haphazard due to the fact that the initial approximation of nerve diameter had to be made without any measurement apparatus. In addition, guide lines had to be present on the template in one form or another, thus introducing undesirable foreign inks into the body of a patient, or alternatively, complicating the production process by embossing or scribing them onto the connector. Also, when the nerve stumps were trimmed, the blades often cut into the connector, thus weakening it and decreasing its efficacy. Furthermore, in the prior system, there was a possibility that the surgeon might trim or cut the "flaps" of the connector thereby creating a danger of stricture to the nerve.

It is accordingly an object of the invention to provide a nerve connector which does not introduce any foreign inks into the body.

Another object of the invention is to minimize the potential for error by eliminating guide lines from the connector.

A further object is to simplify the process of manufacturing the connector by eliminating therefrom both printed and embossed lines.

A still further object of the invention is to eliminate the possibility of accidentally cutting the connector.

A still further object of the invention is to eliminate the need to wrap the nerve in the connector.

Yet another object of the invention is to reduce the size of the connector, thereby minimizing the disturbance to the neighboring body tissues.

SUMMARY OF THE INVENTION

The benefits and advantages of the present invention are achieved by providing an apparatus for reconnecting the proximal and distal stumps of a transected cable-like organ such as blood vessels, tendons, nerves, and the like. The apparatus comprises an elongated template means, a nerve connecting guide means and an elongated connector means for connecting the nerve stumps thereto. The template means includes opposed first and second edges and opposed first and second ends. The nerve connecting guide means also includes a nerve positioning means that extends between the first and second edges. A second pair of stump measuring lines are perpendicular to and intersect the nerve positioning means so as to indicate the preferred position of the respective ends of the nerve stumps. A pair of slot means are provided proximate the respective first and second ends of the template means.

The connector means has first and second edges and is adapted to be slidably inserted within the guide means whereby when the respective ends of the nerve stumps are positioned on the template and the nerve stumps are sutured to the connector means prior to cutting of the nerve stumps and removal of the template means, the reunion of the nerve stumps will be in accordance with the principle of Saint-Venant and the zone of reunion will be free from foreign matter and under absence of stress thereby enhancing healing.

BRIEF DESCRIPTION OF THE DRAWINGS

Some of the features and advantages of the invention having been briefly stated, others will appear from the detailed description which follows, when taken in connection with the accompanying drawings, in which—

FIG. 1 is a plan view of the connector means of the present invention.

FIG. 2 is a plan view of the template means of the present invention.

FIG. 3 is a plan view of the template means with the connector means positioned in the slot means.

FIG. 4 is a plan view of a segment of a transected nerve.

FIG. 5 is a plan view of the distal stump of a transected nerve being sutured through its epineural sheath with the end of the stump being properly located over the stump measuring lines.

DETAILED DESCRIPTION OF THE ILLUSTRATED EMBODIMENT

Figure 6:
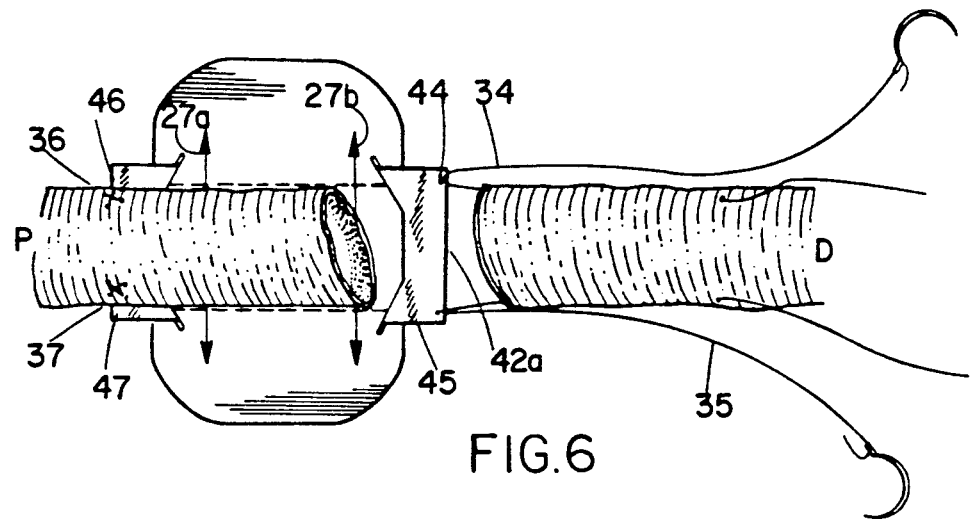
FIG. 6 is a plan view of the proximal stump of a transected nerve sutured through its epineural sheath and sutured to the connector means with the distal end pulled away from the connector means.
Figure 7:
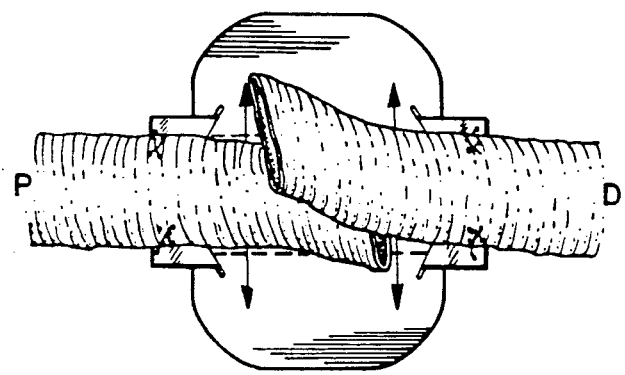
FIG. 7 is a plan view of the distal stump of a transected nerve finally sutured to the connector means, but prior to being trimmed.
Figure 8:
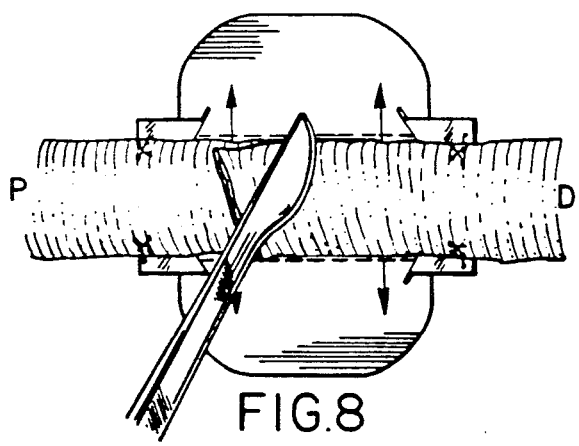
FIG. 8 is a plan view of both stumps of a transected nerve sutured to the connector means and schematically showing the stumps being trimmed.
Figure 9:
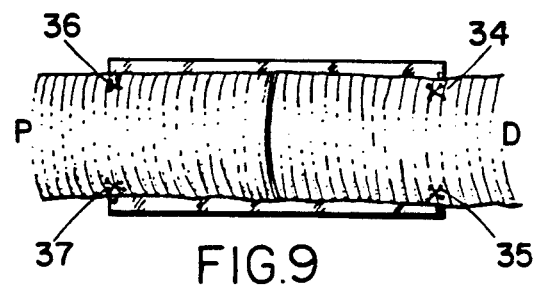
FIG. 9 illustrates the nerve after completion of trimming and alignment.

While the present invention will be described more fully hereinafter with reference to the accompanying drawings, in which a particular embodiment is shown, it is to be understood at the outset that persons skilled in the art may modify the invention herein described while still achieving the favorable results of this invention. Accordingly, the description which follows is to be understood as a broad teaching disclosure directed to persons of skill in the appropriate arts and not as limiting upon the present invention.

Referring now more particularly to the drawings and specifically to FIGS. 1 through 3, the nerve connector of the present invention indicated generally at 10, is there illustrated. The connector comprises an elongate template means 20, nerve connecting guide means 30 and a connector means 40. The template means 20 and the connector means 40 illustrated are selected from a set with the essential difference between the members of the set being that each is scaled to a particular range of nerve diameters. Thus, the size of the template means 20 and the connector means 40 will vary according to the size of the nerve to be reconnected which minimizes the disturbance to any of the surrounding body tissue.

The template means has opposed first and second edges 22a, 22b and opposed first and second ends 24a, 24b. The template means may be made from any thin, preferably inelastic, biocompatible sheet material such as paper or plastics and has a thickness on the order of 0.1 to 0.4 millimeters. Insofar as the length and width are concerned, this is a function of nerve diameter. Biodegradable materials may be employed, but are not necessary as the template 20 is intended to be removed after the nerve stumps are sutured as will be explained more fully hereinbelow.

Formed on the surface of the template means 20 is a nerve connecting guide means or measuring guidelines generally indicated at 30 which in the illustrated embodiment comprises a nerve positioning means 26, a pair of stump measuring lines 27a 27b and first and second slot means 28a 28b.

The nerve positioning means 26 in the illustrated embodiment, take the form of a pair of parallel nerve positioning lines that extend between the first and second ends 24a, 24b. The nerve positioning lines 26 are shown as being dotted and may be applied to the template means 20 by any suitable means such as printing with biocompatible ink or by embossing, in which case the thickness of the template means may be increased as embossing will somewhat weaken the structural integrity of the template means.

The template means 20 also includes a pair of stump measuring lines 27a, 27b that are perpendicular to the nerve positioning lines 26 for indicating the proper positioning of the respective ends of the nerve stumps. As shown in FIGS. 2 and 3, the stump measuring lines 27a, 27b are parallel to the first and second ends 24a, 24b and are solid so that they are easily distinguishable from the nerve positioning lines 26. The stump measuring lines 27a, 27b may be applied to the template means 20 by any suitable means such as printing with biocompatible ink or by embossing in a manner similar to that described above for the nerve positioning lines.

First and second slot means 28a, 28b are associated with the template means 20 proximate the respective first and second ends 24a, 24b. As illustrated in FIGS. 2 and 3, each of the slot means 28a, 28b comprises a pair of oppositely angled short slots or cuts in the respective ends 24a, 24b. The slots are spaced apart so as to facilitate insertion and removal of a connector means 40 to be described.

The apparatus also includes a connector means 40 that is adapted to be slidably received within the slot means 28a, 28b. The connector means 40 has first and second edges 42a, 42b and is made as a 0.1 to 0.4 millimeter thick rectangular sheet of any biocompatible material such as silastic or polyglycolic acid materials. Alternatively, any biodegradable material having a life on the order of about 20 days could be employed. It will be appreciated that the life of the material of choice will vary in accordance with the healing time for the particular structure being reconnected.

The present invention consists of a set of approximately nine sets of nerve template means and connector means, each of which is useful to reconnect a nerve lying within a particular diameter range.

Figure 10:
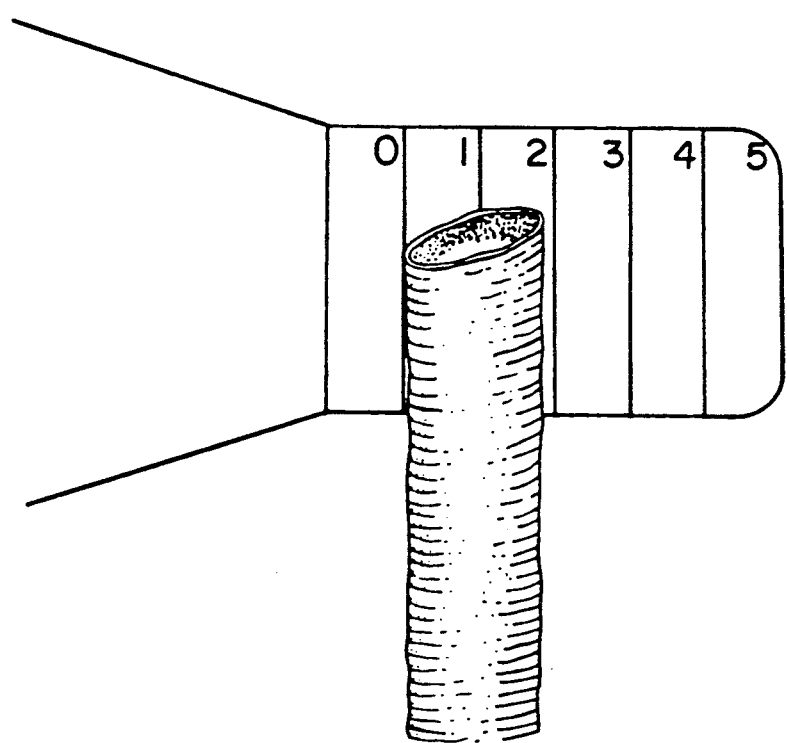
FIG. 10 is a plan view of a nerve diameter measuring apparatus with a nerve stump resting thereon.

In operation, the nerve diameter must be established before the selection of the template means and connector means can be made. This is accomplished by employing a nerve diameter measuring apparatus, one embodiment of which is illustrated in FIG. 10. The nerve diameter measuring apparatus is placed beneath the stump of the transected nerve and one end is aligned with the zero indicator. The surgeon then observes in which field the opposite end of the nerve falls. The fields are marked with a numeral that corresponds to useful range of a template means and connector means for a particular nerve diameter. Once the diameter range is determined, the surgeon then calls for the template an connector means that corresponds to the diameter of the nerve to be repaired.

The use of the invention will be explained with reference to FIGS. 4 through 7. For clarity, certain numerals have been omitted from these figures and the reader is referred to FIGS. 1 through 3 for these numeral designations.

FIG. 4 illustrates the proximal P and distal D stumps of a severed peripheral nerve. During surgical preparation of the nerve, which may also include a chemical preparation and cooling, care should be taken not to disrupt the mesoneurium binding the nerve elements at the top of the stumps so as not to modify their relative orientation. The correct rotational positions of the stumps is determined by careful examination of the tips of the stumps. The correct size nerve connector which includes template means 20 and connector means 40 is then positioned beneath the nerve. If the correct connector has been chosen, the nerve stumps should substantially fill the space between the nerve positioning lines 26. For the purpose of maintaining consistency in the description, it is assumed that the surgeon begins the reunion procedure with the distal stump D.

The reunion process begins with a stitch 34 or other suitable securing means of the appropriate caliber which is passed through the epineurium on one side and through the connector means at point 44. A second stitch 35 is then passed through the epineurium on the other side and through the connector means at point 45 (see FIGS. 5 and 6). These stitches are not tied. Rather, the connector means 40 is pulled away from the distal stump D and placed under the proximal stump P with threads 34, 35 following loosely. The proximal stump P is correctly positioned on connector means 40 by aligning proximal stump P between the nerve positioning means 32a, 32b in such a way that the extremity of the proximal stump P before trimming comes on stump measuring line 27b. Two stitches 36 and 37 are passed through the nerve epineurium of the proximal stump P and through the connector at points 46 and 47 and are tied. The first two stitches 34, 35 are then also pulled tight and tied, bringing the stumps to the desired overlap (see FIG. 7). The proximal stump P and the distal stump D are then both simultaneously trimmed at a point approximately midway between the stump measuring lines. This procedure removes the damaged tips of the nerve stumps and automatically establishes the amount of compression that will exist at the site of reunion.

Those skilled in the art will recognize that sutures represent only one means by which the nerve stumps can be secured to the connector and that clips, biocompatible glue as well as any other securing means or methods compatible with achieving nerve reconnection may be employed with equal efficacy and that sutures as used herein are intended to be exemplary only and are not intended to be limiting on the present invention.

The template is then removed and the wound is closed, leaving the connector means 40 implanted Connector means 30, if made of biodegradable material degrades with time and the rejoined nerve completes the healing process.

Figure 11:
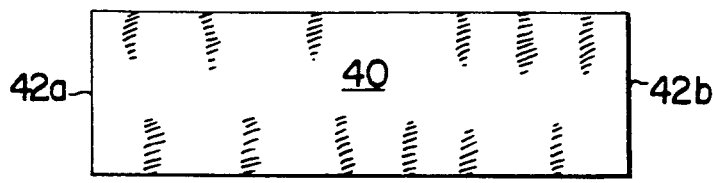
FIG. 11 is a plan view of the connector means of a second embodiment of the invention.
Figure 12:
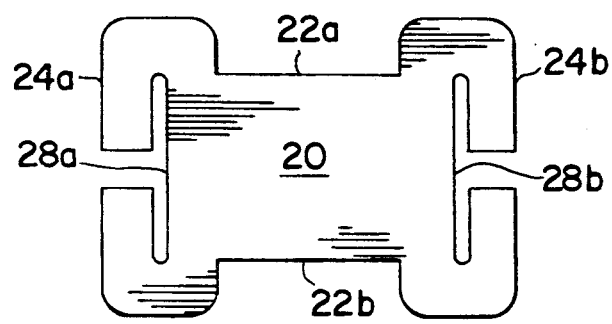
FIG. 12 is a plan view of the template means of a second embodiment of the invention.
Figure 13:
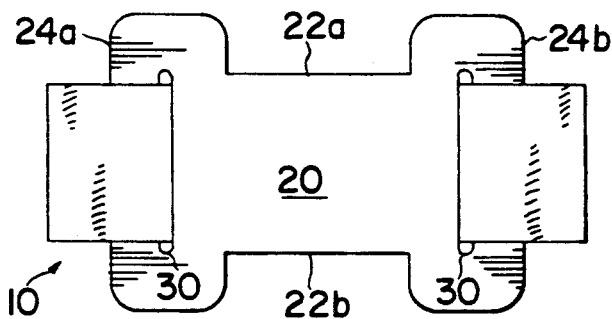
FIG. 13 is a plan view of a second embodiment of the invention and showing the template means positioned within the slot means of the template means.

A second embodiment of the invention is shown in FIGS. 11 through 13. Whenever possible, for the sake of clarity, structures that appear in these figures that are similar to those previously described, bear like reference numerals. Also, where materials, fabrication techniques, dimensions, etc. are substantially similar to those previously described, this information is not repeated.

Referring now specifically to FIGS. 11 through 13, the nerve connector is generally indicated at 10. The connector comprises an elongate template means 20 (FIG. 12) and a connector means 40 (FIG. 11). As previously discussed, the template means 20 and the connector means 40 are selected from a set with the essential difference between set members being that each is scaled to a particular range of nerve diameters. Thus, the size of the template means 20 and the connector means 40 will vary according to the size of the nerve to be reconnected which minimizes the disturbance to the surrounding body tissue.

The template means includes opposed first and second edges 22a, 22b and opposed first and second ends 24a, 24b. Insofar as length and width are concerned, this is a function of nerve diamter. Biodegradable materials may be employed but are not necessary as the template 20 is removed after the nerve stumps are sutured.

The template 20 differs from the template that has been previously described in that the nerve positioning means 26 and the stump measuring lines 27 that were previously indicated by embossing or inking are now defined by the geometry of the template itself. More specifically, the template 20 (FIG. 12) includes opposing first edges 22a and 22b and opposed first and second ends 24a, 24b. The opposing first edges 22a, 22b are divided into a centrally positioned substantially linear section which is narrower than the end portions of the template.

First and second slot means 28a, 28b are associated with the wide section of template means 20 proximate the respective first and second ends 24a, 24b. As illustrated in FIGS. 12 and 13, each of the slot means comprises an elongate cut-out opening in the respective ends 24a, 24b of the template. It will be noted that the length of each of slots 28a, 28b is approximately equal to the width of the connector 40.

The apparatus also includes a connector means 40 that is adapted to be slidably received within slot means 28a, 28b (FIG. 13). The connector means 40 has first and second edges 42a, 42b and is made as a sheet of any biocompatible material, as previously mentioned As best illustrated in FIG. 13, the connector means 40 is adapted to be positioned within the slots 28a, 28b of template 20. The method of suturing the stumps using the connector 40 and the template 20 is essentially identical to that previously described. However, it will be noted that the nerve connecting guide means or measuring guidelines (reference numeral 30 of the previously described embodiment) have been replaced by the edges of the slots themselves.

Similarly, the nerve positioning means (reference numeral 26 of the previously described embodiment) is also defined by the narrow portion of the template 20. This template configuration eliminates the need for inking or embossing the nerve positioning means and the stump measuring lines thus substantially simplifying fabrication of the device.

Figure 14:
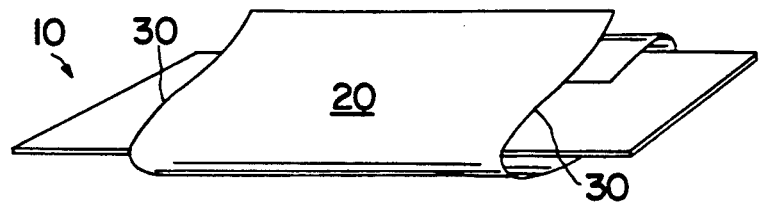
FIG. 14 is a perspective view of a third embodiment of the invention showing a guide means wrapped around the template means.

A third embodiment of the invention, further simplified from these previously described, is illustrated in FIG. 14. The embodiment comprises a template means 20 which is preferably fabricated from metal foil such as aluminum. The template 20 has opposite ends 24a, 24b that define nerve connecting guide means.

The template 20 is wrapped tightly around and is centered in the central portion of the connector 40. In this case, the referenced nerve connector guide means 30 is defined by the four corners of the template where it contacts the connector as indicated in FIG. 14. The metal foil serves to protect the underlying connector 40 when the nerve stumps are trimmed by the surgeon. The method of rejoining the nerve stumps remains essentially identical to that already described and need not be repeated here in detail.

The foregoing embodiment is to be considered illustrative, rather than restrictive of the invention, and those modifications which come within the meaning and range of equivalence of the claims are to be included therein.

That which is claimed is:

1. An apparatus for reconnecting the proximal and distal stumps of a transected cable-like organ such as blood vessels, tendons, nerves and the like and comprising:
   (a) an elongate template means having opposed first and second edges and opposed first and second ends,
   (b) a nerve connecting guide defined by the geometry of said template means comprising:
      (i) a nerve positioning means defined by the longitudinal axis of said template means,
      (ii) nerve connecting guide means located proximate the respective ends of said template for indicating the positioning of the respective ends of the nerve stumps,
   (c) a connector means adapted to be slidably received within said template means, whereby when the respective ends of the nerve stumps are positioned on the template and the nerve stumps are sutured to the connector means prior to cutting of the nerve stumps and removal of the template means, the reunion of the nerve stumps will be in accordance with a postulate derived from the principle of Saint-Venant and the zone of reunion will be free of foreign matter and substantially free of stress thereby enhancing healing.

2. An apparatus according to claim 1 further including first and second slot means associated with said template means, said first slot means proximate the first end and said second slot means proximate the second end and wherein said first and second slot means define said nerve connecting guide means.

3. An apparatus according to claim 1 wherein each of said first and second slot means comprises a pair of cut-out portions perpendicular to the longitudinal axis of said template means.

4. The apparatus according to claim 1 wherein said template means is in overlying relation to said connector means and said template means acts so as to protect said connector means from inadvertently being cut when the nerve is cut.

5. A method for reconnecting first and second stumps of a transected cable-like organ, such as nerves, blood vessels, tendons and the like, comprising the steps of:
   (a) locating below the first stump of the transected structure to be reconnected a connector and a removable template, the template defining a nerve connecting guide;
   (b) securing a first predetermined connecting guide measured length of the first stump to the connector at a point removed from the tip of the stump;
   (c) locating the second stump of the structure to be reconnected on the connector and the template and securing a second predetermined connecting guide measured length of the second stump to the connector at a point removed from the tip of the second stump and spaced some predetermined distance opposite from the point at which the first stump was secured;
   (d) trimming a connecting guide measured length of tissue from the tip of each of the stumps to provide some third predetermined length of stump overlapping when the tips ends of said stumps are placed end-to-end, the third predetermined length corresponding to a desired amount of compression in the reconnected structure at the site of the reunion of the stumps;
   (e) removing the template from beneath the stumps;
   (f) placing the stumps in longitudinal alignment on the connector with the tips thereof in abutment so that the zone of reunion is free of foreign matter.

6. The method of claim 5 wherein:
   (a) said transected cable-like structure comprises a nerve; and
   (b) said stumps comprise transected stumps of said nerve.

7. The method of claim 6 wherein said nerve stumps are secured by sutures through the perineurium of said nerve.

8. The method of claim 5 wherein:
   (a) said template is formed of a substantially rectangular sheet of material having nerve connecting guide defined thereby; and
   (b) said first, second and third predetermined lengths are measured by said nerve connecting guide defined by the geometry of said template on which said stumps are located and said points of securement on said connector are determined utilizing said nerve connecting guide means.

9. The method of claim 5 wherein said material is a thin inelastic sheet material.

10. The method of claim 5 wherein the first and second stumps of the structure to be reconnected are secured to the connector approximately 1.5 to 2.0 trimmed structure diameters away from the respective stumps so as to be substantially free of stress and in accordance with the postulate derived from the principal of Saint-Venant.

11. The method of claim 5 wherein the first and second predetermined length of said stumps secured to the connector are approximately 1.5 to approximately 2.0 structure diameters.

12. A method for reconnecting first and second stumps of a transected nerve comprising the steps of:
(a) locating proximate the site of reunion a nerve connector and a template, both the connector and the template being formed of flexible inelastic, thin sheet material, the template having spaced apart opposed first and second defined edges and defining nerve connecting guide;
(b) connecting at selected points to a first edge of the connector with sutures through the perineurium of said first stump, a first predetermined nerve connecting guide means measured length of the first stump extending towards the second edge and with the top of the first stump being beyond the midpoint between the edges;
(c) locating the connector in position beneath the second stump so that the sutures through the perineurium of the first stump loosely connect said first stump to the connector;
(d) connecting at other selected points to a second edge of said connector with sutures through the perineurium of the second stump of a second predetermined nerve connecting guide means measured length of the second stump extending towards aid first edge and with the tip of said second stump being beyond the midpoint between said edges;
(e) tying the sutures connecting the second stump with said connector
(f) tightening the sutures securing said first stump to said connector so that said first stump is pulled towards the connector and the tips of said stumps are brought in overlying relation;
(g) tying the sutures connecting the first stump with the connector;
(h) trimming tissue from the tips of each of said stumps to establish a precise predetermined nerve connecting guide means measured length of said stumps;
(i) removing the template from beneath the stumps;
(j) placing the tips of said stumps into abutment with the longitudinal axis of said stumps in substantial alignment at the site of reunion.

13. The method of claim 12 wherein trimming of both stumps is done simultaneously.

* * * * *